United States Patent
Piippo Svendsen et al.

(10) Patent No.: US 8,795,304 B2
(45) Date of Patent: Aug. 5, 2014

(54) ATHERECTOMY DEVICE, SYSTEM AND METHOD HAVING A BI-DIRECTIONAL DISTAL EXPANDABLE ABLATION ELEMENT

(75) Inventors: Cassandra A. Piippo Svendsen, Hugo, MN (US); Daniel J. Lee, Monticello, MN (US); Rachel E. DeSmidt, Madison, WI (US); Jesse C. Darley, Madison, WI (US)

(73) Assignee: Cardiovascular Systems, Inc., St. Paul, MN (US)

( * ) Notice: Subject to any disclaimer, the term of this patent is extended or adjusted under 35 U.S.C. 154(b) by 259 days.

(21) Appl. No.: 12/817,354

(22) Filed: Jun. 17, 2010

(65) Prior Publication Data

US 2011/0144671 A1    Jun. 16, 2011

Related U.S. Application Data

(60) Provisional application No. 61/218,206, filed on Jun. 18, 2009.

(51) Int. Cl.
*A61B 17/22* (2006.01)
*A61B 17/32* (2006.01)
*A61B 17/3207* (2006.01)

(52) U.S. Cl.
CPC .............. *A61B 17/320758* (2013.01); *A61B 2017/320028* (2013.01); *A61B 17/32075* (2013.01); *A61B 2017/320775* (2013.01)
USPC ........................................................ 606/159

(58) Field of Classification Search
USPC .............. 604/19, 22, 104–109; 606/108, 159, 606/167, 170, 171, 180, 191, 194, 198, 200
See application file for complete search history.

(56) References Cited

U.S. PATENT DOCUMENTS

| | | | |
|---|---|---|---|
| 4,771,782 A * | 9/1988 | Millar | 600/486 |
| 4,779,316 A * | 10/1988 | Cherry et al. | 74/603 |
| 4,919,133 A | 4/1990 | Chiang | |
| 4,966,604 A | 10/1990 | Reiss | |
| 5,009,659 A | 4/1991 | Hamlin et al. | |
| 5,030,201 A | 7/1991 | Palestrant | |
| 5,100,426 A * | 3/1992 | Nixon | 606/170 |
| 5,178,625 A | 1/1993 | Groshong | |
| 5,197,971 A * | 3/1993 | Bonutti | 606/192 |
| 5,224,945 A | 7/1993 | Pannek, Jr. | |
| 5,282,484 A | 2/1994 | Reger | |
| 5,318,576 A | 6/1994 | Plassche, Jr. et al. | |

(Continued)

OTHER PUBLICATIONS

International Search Report from PCT/US2010/039116 dated Aug. 18, 2010.

*Primary Examiner* — Ashley Fishback
(74) *Attorney, Agent, or Firm* — Winthrop & Weinstine, P.A.

(57) ABSTRACT

The invention provides a rotational atherectomy system, device and method comprising a bi-directional drive shaft with a flexible ablation element disposed at the distal end of the drive shaft. The flexible ablation element comprises a first retracted position for insertion into vasculature and a second expanded position for ablation, i.e., cutting, sanding and/or grinding. The ablation element comprises more than one flexible finger or blade which allows changing, in certain embodiments, of curvature radius to fit inside a deployment catheter and/or enlarge to the diameter of larger lumens, up to at least 9 mm in diameter. Bi-directional rotation of the expanded ablation element allows cutting in one rotational direction and grinding and/or sanding in the opposite rotational direction.

12 Claims, 7 Drawing Sheets

(56) References Cited

U.S. PATENT DOCUMENTS

| | | | |
|---|---|---|---|
| 5,320,627 A | 6/1994 | Sorensen et al. |
| 5,376,100 A | 12/1994 | Lefebvre |
| 5,556,405 A | 9/1996 | Lary |
| 5,556,408 A | 9/1996 | Farhat |
| 5,827,304 A | 10/1998 | Hart |
| 6,096,054 A | 8/2000 | Wyzgala et al. |
| 6,503,261 B1 | 1/2003 | Bruneau et al. |
| 6,565,588 B1 | 5/2003 | Clement et al. |
| 6,800,083 B2 | 10/2004 | Hiblar et al. |
| 6,800,085 B2 | 10/2004 | Selmon et al. |
| 6,818,001 B2 | 11/2004 | Wulfman et al. |
| 7,252,674 B2 | 8/2007 | Wyzgala et al. |
| 7,322,957 B2 | 1/2008 | Kletschka et al. |
| 7,344,535 B2 | 3/2008 | Stern et al. |
| 2001/0018596 A1 | 8/2001 | Selmon et al. |
| 2001/0020172 A1 | 9/2001 | Selmon et al. |
| 2002/0077638 A1 | 6/2002 | Kadavy et al. |
| 2002/0147458 A1 | 10/2002 | Hiblar et al. |
| 2003/0144677 A1 | 7/2003 | Lary |
| 2007/0118165 A1 | 5/2007 | DeMello et al. |
| 2007/0213752 A1 | 9/2007 | Goodin et al. |
| 2008/0039727 A1 | 2/2008 | Babaev |
| 2008/0228208 A1 | 9/2008 | Wulfman et al. |
| 2008/0228209 A1 | 9/2008 | DeMello et al. |
| 2009/0125043 A1 | 5/2009 | Dehnad |
| 2009/0149877 A1 | 6/2009 | Hanson et al. |
| 2009/0270893 A1 * | 10/2009 | Arcenio ................. 606/170 |

* cited by examiner

Fig. 5F

ATHERECTOMY DEVICE, SYSTEM AND METHOD HAVING A BI-DIRECTIONAL DISTAL EXPANDABLE ABLATION ELEMENT

CROSS-REFERENCE TO RELATED APPLICATIONS

The present application claims priority to provisional application No. 61/218,206, filed on Jun. 18, 2009 under the title, "OVERLAPPING EXPANDING LEAF LARGE VESSEL ATHERECTOMY DEVICE", the entire content of which is incorporated by reference herein.

STATEMENT REGARDING FEDERALLY SPONSORED RESEARCH OR DEVELOPMENT

Not Applicable

BACKGROUND OF THE INVENTION

1. Field of the Invention

The invention relates to devices and methods for removing tissue from body passageways, such as removal of atherosclerotic plaque from arteries, utilizing a rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer under the endothelium of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic or occluding material. If left untreated, this occluding material can cause angina, hypertension, myocardial infarction, strokes and the like.

Rotational atherectomy procedures have become a common technique for removing such occluding material in blood vessels. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove occluding material. In one type of device, such as that shown in U.S. Pat. No. 4,990,134 (Auth), a concentrically shaped ellipsoidal burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently, since the burr is of a fixed resting diameter, more than one size burr must be utilized to open an artery to the desired diameter.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., rotational speeds within the range of about 20,000-200,000 rpm. Essentially, the center of mass offset from the rotational axis of the drive shaft would result in development of significant and undesirable centrifugal force, exerting too much pressure on the wall of the artery and creating too much heat and excessively large particles. As with Auth, the burr size is fixed and may require using more than one size burr to open the subject lumen to the desired diameter.

U.S. Pat. No. 6,132,444 (Shturman) and U.S. Pat. No. 6,494,890 (Shturman) both commonly assigned to the assignee of the instant application, disclose, inter alia, an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The orbital rotational motion is primarily due to the offset of the center of mass of the enlarged eccentric section from the drive shaft's rotational axis. Since the enlarged eccentric section may comprise drive shaft wires that are not bound together, the enlarged eccentric section of the drive shaft may flex during placement within the stenosis or during high speed operation. This flexion allows for a larger diameter opening during high speed operation than the resting diameter of the enlarged eccentric section. The disclosures of U.S. Pat. Nos. 6,132,444 and 6,494,890 are each hereby incorporated by reference in their entirety.

Generally speaking, current atherectomy devices give modest luminal gains; up to approximately 6 mm is the limit for most devices, though the devices manufactured according to U.S. Pat. Nos. 6,132,444 and 6,494,890, and variations thereof, provide potential working diameters during high-speed rotation up to and in excess of 6 mm. However, for most devices, full treatment of an obstructed lumen with diameter larger than approximately 6 mm requires subsequent procedural steps such as ballooning and/or stenting.

Accordingly, it would be desirable to provide an atherectomy device, system or method that combines a small crossing profile (less than 6 Fr) and the ability to fully treat occlusions in vessels with diameters up to 9 mm. The present invention addresses this need.

BRIEF SUMMARY OF THE INVENTION

The invention provides a rotational atherectomy system, device and method comprising a bi-directional drive shaft with a flexible ablation element disposed at the distal end of the drive shaft. The flexible ablation element comprises a first retracted position for insertion into vasculature and a second expanded position for ablation, i.e., cutting, sanding and/or grinding. The ablation element comprises more than one flexible finger or blade which allows changing, in certain embodiments, of curvature radius to fit inside a deployment catheter and/or enlarge to the diameter of larger lumens, up to at least 9 mm in diameter. Bi-directional rotation of the expanded ablation element allows cutting in one rotational direction and grinding and/or sanding in the opposite rotational direction.

An object of the invention is to provide an atherectomy device that comprises a first retracted position for insertion into vasculature and a second expanded position for abrasion.

Another object of the invention is to provide an atherectomy device with a crossing retracted profile with a smaller diameter than its working expanded profile, i.e., less than 6 French crossing retracted profile and a working expanded profile that also can fully abrade occluding material in vessels having diameters of up to 9 mm.

Another object of the invention is to provide an atherectomy device with a crossing retracted profile having a smaller diameter than the resting expanded profile, and wherein the resting expanded profile comprises a smaller diameter than the rotating working expanded profile.

Another object of the invention is to provide an atherectomy device that is bi-directionally rotatable and wherein rotation in one direction allows cutting while rotation in the opposite direction allows grinding and/or sanding.

Another object of the invention is to provide an atherectomy device that automatically achieves the second expanded position.

Another object of the invention is to provide an atherectomy device that provides an actuating device for achieving the second expanded position.

Another object of the invention is to provide an atherectomy device that provides an actuating device comprising a symmetric profile which results in a correspondingly symmetric second expanded position.

Another object of the invention is to provide an atherectomy device that provides an actuating device comprising an asymmetric profile which results in a correspondingly asymmetric second expanded position.

Another object of the invention is to provide an atherectomy device that provides an actuating device comprising an asymmetric profile which results in a correspondingly asymmetric second expanded position, wherein the actuating device comprises a wedge attached to a wire and having an asymmetric profile correspondent with the asymmetric second expanded position.

Another object of the invention is to provide an atherectomy device that provides the ablation element comprising distal fingers formed from a plurality of longitudinal slots, wherein the distal fingers are biased radially outwardly to achieve the second expanded position which may comprise a symmetric or asymmetric profile, wherein the fingers are arranged adjacent one another, each finger having a longitudinal profile that is complementary with the longitudinal profile of the adjacent fingers, thereby allowing the ablation element to achieve a minimum profile when in the first retracted position.

Another object of the invention is to provide an atherectomy device that provides the ablation element comprising distal fingers formed from a plurality longitudinal slots and arranged in an interleaved and overlapping manner, wherein the distal fingers are biased radially outwardly to achieve the second expanded position which may comprise a symmetric or asymmetric profile.

Another object of the invention is to provide an atherectomy device comprising the radially expandable distal fingers stopping short of the distal end of the flexible tube.

Another object of the invention is to provide an atherectomy device comprising abrasive surfaces that may grind and/or sand occluding material when rotated and/or axially translated.

Another object of the invention is to provide an atherectomy device comprising radially expandable distal fingers that are symmetrically arranged around the axis of rotation of the drive shaft.

Another object of the invention is to provide an atherectomy device comprising radially expandable distal fingers that are asymmetrically arranged around the axis of rotation of the drive shaft.

Another object of the invention is to provide an atherectomy device comprising radially expandable distal fingers comprising symmetric mass distribution around the axis of rotation of the drive shaft.

Another object of the invention is to provide an atherectomy device comprising radially expandable distal fingers comprising asymmetric mass distribution around the axis of rotation of the drive shaft.

Another object of the invention is to provide an atherectomy device comprising the ability to capture material removed during the atherectomy procedure for subsequent removal from the vessel.

Another object of the invention is to provide a system and methods to achieve, inter alia, the above objectives.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
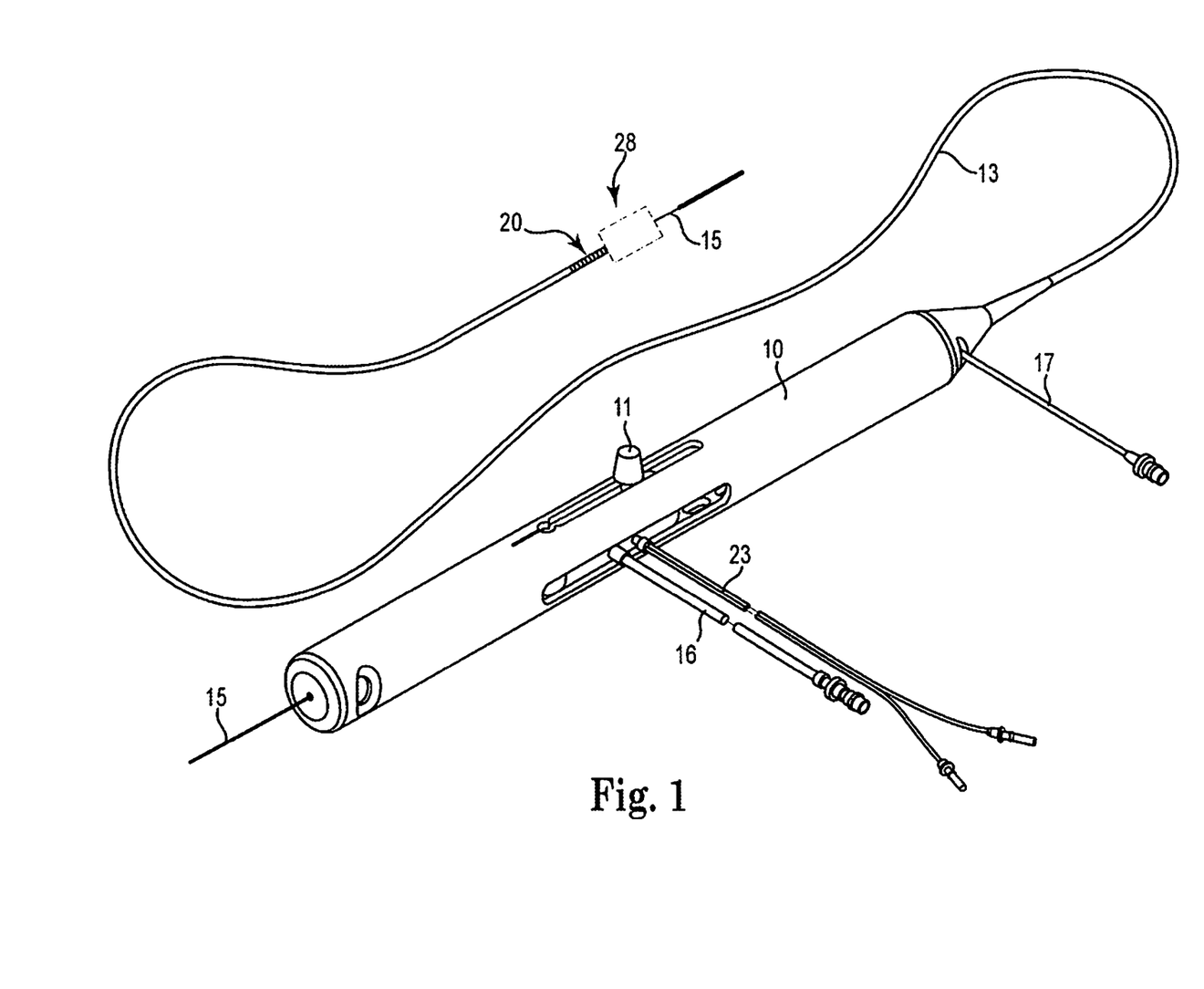
FIG. 1 is a perspective view of one embodiment of the present invention.

FIG. 1 is a schematic drawing of one embodiment of a typical atherectomy device. FIG. 1 illustrates one embodiment of a rotational atherectomy system and device of the present invention. The system includes a handle portion 10, an elongated, flexible introducer catheter 13 having a lumen (not shown) with a flexible and rotatable drive shaft 20 rotatable and axially translatable within the lumen of catheter 13, the drive shaft 20 having an ablating element 28 (illustrated with dashed lines) at its distal end. The detailed description of ablating element 28 is discussed below. Drive shaft 20 further comprises a lumen (not shown), within which guide wire 15 may be in operative communication and axially and rotatably moveable. The device and system is illustrated with guide wire 15 in position, i.e., extended through and distal to ablating element 28, however, the skilled artisan will recognize that atherectomy procedures using the present invention may be completed satisfactorily either with or without guide wire 15 extended through ablating element 28. Moreover, drive shaft 20 is in rotatable and axially translatable and operative communication with introducer catheter 13 and introducer catheter's lumen (not illustrated). The ablating element 28 is illustrated as extending distally from introducer catheter 13, illustrating that the drive shaft 20 and the introducer catheter 13 are translated axially relative to one another as well as rotatably moveable relative to one another. This relative axial translation may be achieved by pushing the drive shaft 20 distally, pulling the introducer catheter 13 proximally, or a combination thereof.

A fluid supply line 17 may be provided for introducing a cooling and lubricating solution (typically saline or another biocompatible fluid) into the catheter 13 wherein fluid supply line is operatively connected with catheter. In certain embodiments warming and/or cooling biocompatible fluid may be introduced and/or urged into the catheter 13 via fluid supply line. For the present invention, the fluid supply line 17 may also supply therapeutic substances, e.g., restenosis drugs.

The handle 10 desirably contains a turbine (or similar rotational drive mechanism, e.g., an electric motor) for rotating the drive shaft 20 at very low to relatively high speeds in a single rotational direction, and is further capable of rotating drive shaft 20 in the opposing rotational direction and/or in reciprocating rotational directions. The handle 10 typically may be connected to a power source, such as compressed air delivered through a tube 16. A pair of fiber optic cables 23 may also be provided for monitoring the speed of rotation of the turbine and drive shaft 20 (details regarding such handles and associated instrumentation are well known in the industry. The handle 10 also desirably includes a control knob 11 for advancing and retracting the drive shaft 20 with respect to the catheter 13 and the body of the handle 10.

There are several ways to rotate and control the drive shaft and fluid flow during operation. In most cases, a turbine or electric motor is attached to the drive shaft at or near the proximal end of the drive shaft. A suitable control system and method for such a motor is disclosed in U.S. Pat. No. 7,174,240, titled "Control system for rotational angioplasty device", and published on Jun. 26, 2003 as U.S. Patent Application Publication No. US 2003/0120296 A1, which is incorporated by reference herein in its entirety.

Other methods of urging drive shaft 20 rotation are possible as well. For instance, the user can directly rotate the drive shaft by hand. As another example, the user can turn a crank connected to the drive shaft. As a further example, the user can turn a crank, with the crank driving a geared system that scales up the rotational speed of the drive shaft by a particular factor over the rotational speed of the crank. Other suitable rotation-producing systems are possible as well.

Debris created during the atherectomy procedure using ablation element 28 may be captured by a suction applied within the lumen of drive shaft 20. Alternatively, such debris may be captured distal to the ablation site using known distal embolic protective devices. Still more alternatively, a one-way valve may be employed within the lumen of catheter tube 20 that, in conjunction with a suction force produced by known means, may be used to capture debris therein.

As used herein, the term "ablation" shall be defined as meaning using ablating element 28, and equivalents thereof, to achieve cutting, sanding and/or grinding of tissue occluding a biological lumen, wherein the ablation is achieved by side-to-side motion, rotational motion, reciprocating rotational motion, forward and/or backward motion, i.e., proximal and/or distal motion also known as axial translation, whether resulting from manual, automated, motorized (turbine, electric or other) and/or vibrational means.

Figure 2:
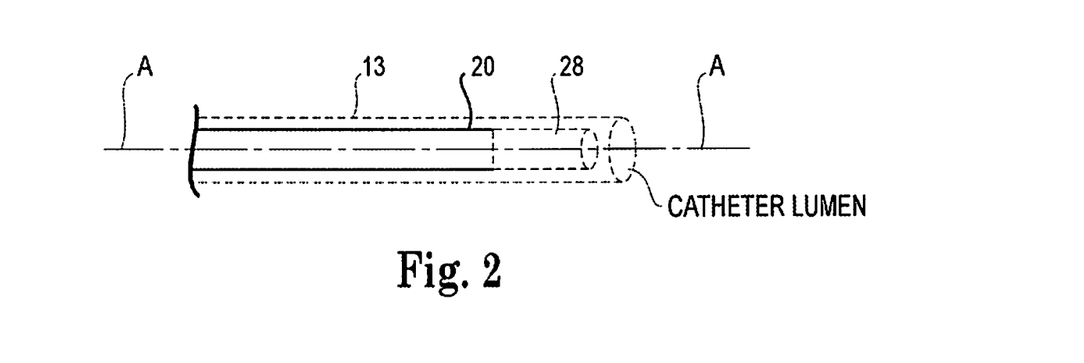
FIG. 2 is a partial cutaway side view of one embodiment of the present invention.

With reference now to FIG. 2, one embodiment of the present invention is illustrated generally with ablating element 28 in a first, deformed and retracted position and illustrated in dashed lines to indicate the general nature of ablating element 28; individual embodiments of ablating element 28 are discussed in detail infra. In this retracted position, the ablating element 28 is within the lumen of introducer catheter 13 and collinear with longitudinal and rotational axis A. The illustrated embodiment thus comprises an ablating element 28 which is deformed when retracted within lumen 13 and undeformed when allowed to expand when translated axially distally out of lumen 13. As will be further discussed infra, alternative embodiments of ablating element 28 may comprise the retracted configuration as being undeformed and the expanded configuration being the deformed state.

Figure 3A:
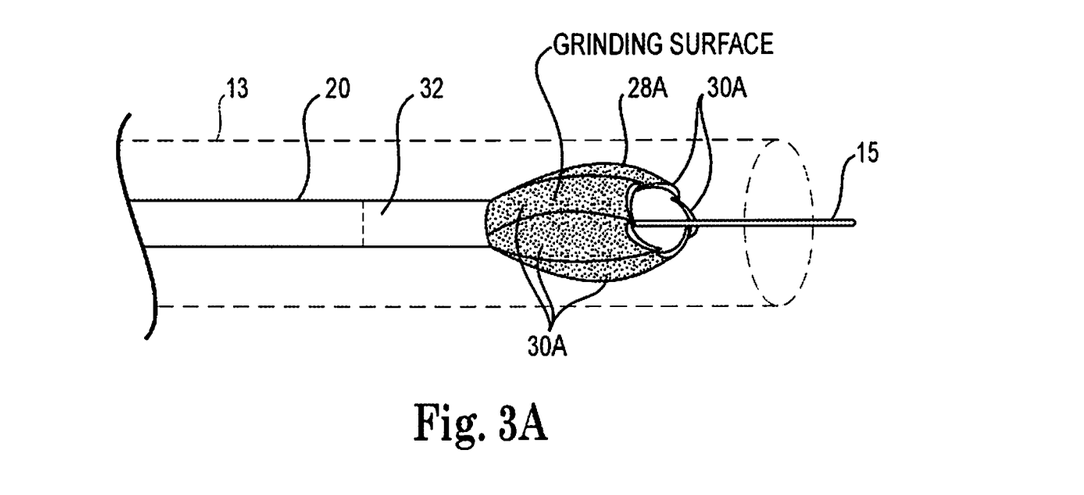
FIG. 3A is a partial cutaway side view of one embodiment of the present invention.
Figure 3B:
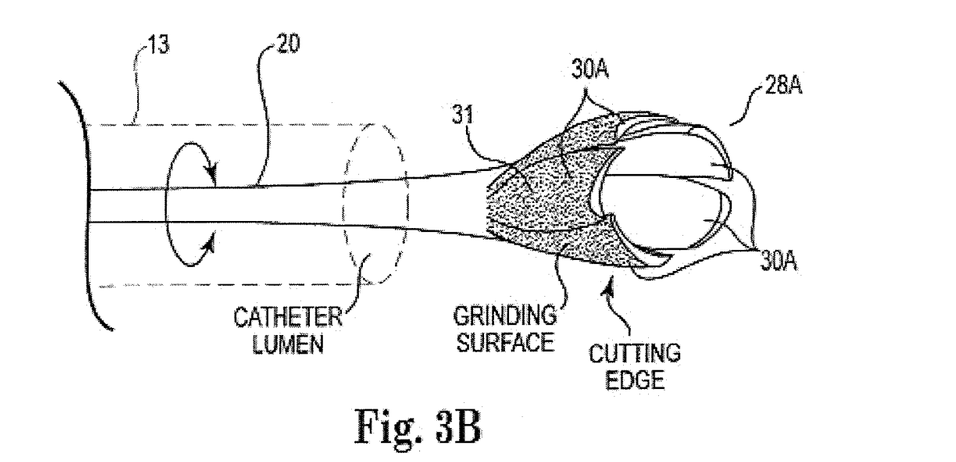
FIG. 3B is a partial cutaway side view of one embodiment of the present invention.

A particular embodiment of ablating element 28A is shown in greater detail in its first deformed and retracted position in FIGS. 3A and 3B. FIG. 3A provides one embodiment of ablating element 28A in its first deformed and retracted position, with at least two radially expandable fingers 30A collapsed and folded against one another in a partially overlapping and interleaved manner. The ablating element 28A may comprise a separately manufactured element that is subsequently fixedly attached to the most distal end of drive shaft 20. Such a configuration may comprise a tube 32 that is fixedly attached to the distal end of drive shaft 20, with the ablating element 28A and its fingers 30 formed and defined from tube 32. Alternatively, ablating element 28A may not comprise tube 32, wherein the ablating element 28A is attached directly to drive shaft 20; this configuration is shown in FIG. 3B.

The embodiments illustrated in FIGS. 3A and 3B illustrates at least two radially expandable fingers 30A which, when in the first deformed and retracted position, overlap and are interleaved against the fingers 30A directly adjacent on either side. Each finger 30 comprises an external surface 34 and a cutting edge defined by one side edge and a grinding surface on the external surface 34 as illustrated. The cutting edge of each finger 30A may be hidden beneath the next adjacent finger 30A when in the first deformed and retracted position as shown in FIG. 3A. The ablating element 28A is held in the first deformed and retracted position by the forces exerted on it by the walls of the catheter lumen.

When drive shaft 20 and ablating element 28A are translated axially and distally relative to catheter 13 to the point where the ablating element 28A is no longer constrained by the walls of the catheter lumen, the ablating element's fingers 30A expand automatically by known methods to a second expanded position as illustrated in FIG. 3B. The skilled artisan will recognize that such an automatic expansion and return to an undeformed state may be achieved through use of heat setting and/or shape memory alloys and/or other methods and materials. Thus, the ablating element 28A, specifically fingers 30A are preferably flexible and may be constructed from virtually any material capable of elastic characteristics, but operating within the selected material's range of elastic and non-plastic deformation. Preferably, shape memory materials such as Nitinol may be used to achieve the desired shaping of fingers 30A in a manner well known to the skilled artisan. Releasing the fingers 30A from constriction within, e.g, the catheter 13 allows the ablating element 28A to automatically resume its non-deformed and shaped form.

Examples of superelastic metal alloys, including Nitinol, which are usable to form certain embodiments of the ablating element 28A of the present invention are described in detail in U.S. Pat. No. 4,665,906. The disclosure of U.S. Pat. No. 4,665,906 is expressly incorporated herein by reference insofar as it describes the compositions, properties, chemistries, and behavior of specific metal alloys which are superelastic within the temperature range at which the ablating element 28A of the present invention operates, any and all of which superelastic metal alloys may be usable to form the ablating element 28A.

In addition to the constriction and release of the all embodiments of ablating element 28 discussed herein, including but not limited to the particular embodiment illustrated by ablating element 28A formed from shape memory alloy from the lumen of introducer catheter 13, controlled application of heating and cooling methods may be used to induce the ablating element 28A to deform to substantially linear retracted position or undeform to its radially expanded position. Thus, the operator may apply heat to the ablating element 28A by bathing the ablating element 28A in a heated and/or heat-controlled (heatable and/or coolable) physiologically compatible fluid (e.g., saline, Ringer's Solution, etc.) that is introduced via the lumen of introducer catheter 13 and/or through the lumen of drive shaft 20. By controlling the temperature of the fluid introduced, either warming or cooling, the temperature of the ablating element 28A is similarly controlled to affect its shape in urging the ablating element 28A to/from retracted position to expanded position and back to retracted position. Such methods may be used and applied to all fingers 30A to achieve a symmetric automatic expanded position or, alternatively, may be applied to select fingers 30A to achieve an asymmetric automatic expanded position.

Alternatively, the operator may control the retracted versus expanded positions of ablating element 28A by controlling the temperature of ablating element 28A by passing current through the guide wire 15 from its proximal end to allow the ablating element 28A to controllably achieve its undeformed and expanded position due to the heat generated in ablating element 28A by the current applied as described. Alternatively, a cooling effect may be realized by using a Peltier device as is well known in the art to return the ablating element 28A to its deformed and retracted position. As those skilled in the art will recognize, the application of electrical current to ablating element 28A may be accomplished by attaching one or two leads operatively connected with ablating element 28A. Again, such methods may be used and applied to all fingers 30A to achieve a symmetric expanded position or, alternatively, may be applied to select fingers 30A to achieve an asymmetric expanded position.

Throughout this specification, reference is made to a first retracted position and a second expanded position. This is not to define the first and second positions as discreet positions, but rather, the present invention comprises first and second positions as variable and controllable positions. Further, within a single embodiment, several positions may be achieved while remaining within the scope of the terms "first, retracted" and "second, expanded" positions.

Turning now to FIG. 3B, the ablating element 28A is illustrated as axially translated distally away from catheter 13, thereby freeing the fingers 30A from being constrained by the walls of the catheter lumen. Thus, ablating element 28A is in a second expanded position, whereby the fingers 30A automatically expand radially to expose a cutting edge on one side and a grinding surface on the external surface 31.

Extension by the operator of the ablating element 28A beyond the distal end of catheter 13 automatically allows expansion of the ablating element 28A to a second expanded position as the fingers 30A expand either to the maximum preset diameter and state or up to the point where the fingers 30A may encounter either the vessel wall or the occluding material. Ablating element 28A experiences an elastic and non-plastic deformation to achieve the second expanded position within the subject lumen. Thus, as discussed briefly above, the expanded diameter of the ablating element 28B in the second expanded position is sufficient to accommodate vessels having diameters as large as 9 mm. Thus, the ablating element 28A is preferably constructed so that, when released from deformation, it automatically moves to assume a position that is in a pressing and atraumatic operative engagement with the inner lumen wall.

Thus, at least a portion of the fingers 30A may operatively press against the inner wall of the lumen, more preferably against occluding material within the lumen. This creates an opposing biasing force that is transmitted to, and ultimately exerted by, the outer the fingers 30A against the inner wall of the lumen, preferably in close proximity to the occluding material that is to be directionally ablated. In this manner, the cutting edge and grinding surfaces of the fingers 30A are biasingly forced against the occluding material in preparation for directional rotational ablation, i.e., cutting and/or grinding.

The drive shaft 20 and ablating element 28A attached thereto are bi-directional so that the operator may direct rotation of the ablating element 28A either in a clockwise or a counter clockwise direction. As illustrated, a clockwise rotation will present the grinding surface to the occlusion while effectively keeping the cutting edge away from the occlusion. Alternatively, a counter clockwise rotation in the illustrated embodiment will present the cutting edge to the occlusion while still allowing the grinding surface to grind and/or sand the occlusion during rotation. This is because the grinding surface is located on the external surface 31 of each finger 30A and may engage the occluding material when ablating element 28A is rotated in either direction. The skilled artisan will readily recognize that the cutting edge and the grinding surface of the fingers 30A illustrated may be swapped such that a clockwise rotation presents the grinding surface to the occlusion while effectively keeping the cutting edge away from the occlusion and counter clockwise rotation allows presentation of both the cutting edge and grinding surface to the occlusion.

Axial translation of the drive shaft 20 and ablating element 28A will result in reintroduction of the ablating element 28A and fingers 30A into the lumen of the catheter, thereby urging the fingers 30A back into the interleaved configuration of the first deformed and retracted position.

Figure 4:
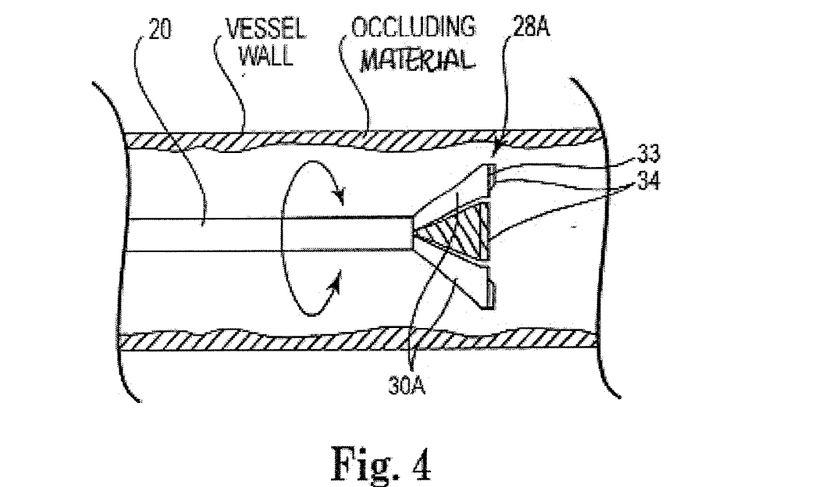
FIG. 4 is a cutaway side view of one embodiment of the present invention.

FIG. 4 provides another embodiment of ablating element 28A wherein fingers 30A each comprise an atraumatic lip 33 defined on the distal surface. This lip 33 may create another cutting surface 34 which may be used to engage occluding material when the operator pushes the drive shaft 20 and ablating element 28A distally against the occlusion when the ablating element 30A. Because the lip 33 comprises a profile which directs the cutting surface 34 away from the vessel wall, the lip 33 serves to minimize trauma to the wall.

As briefly discussed above, all embodiments of ablating element 28 discussed herein, including without limitation ablating element 28A, may serve another function in the atherectomy procedure when moving from the second expanded position to the first retracted position after ablation is complete. Debris created during the procedure may be trapped within the fingers 30A as they are retracted and subsequently removed from the patient's vasculature.

Figure 5A:
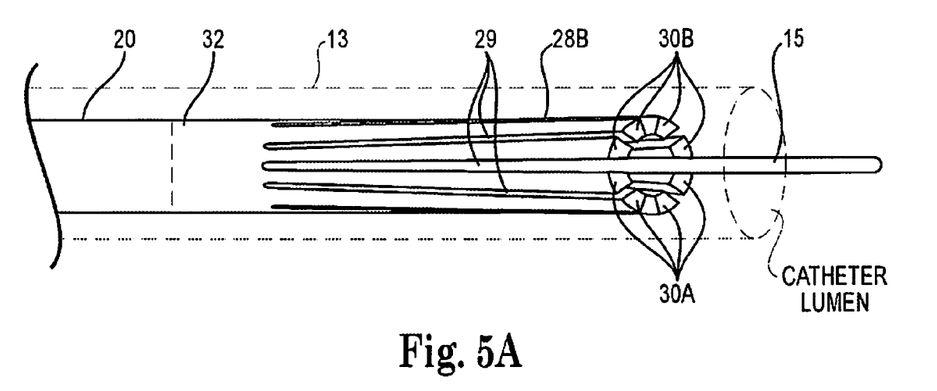
FIG. 5A is a partial cutaway side view of one embodiment of the present invention.
Figure 5B:
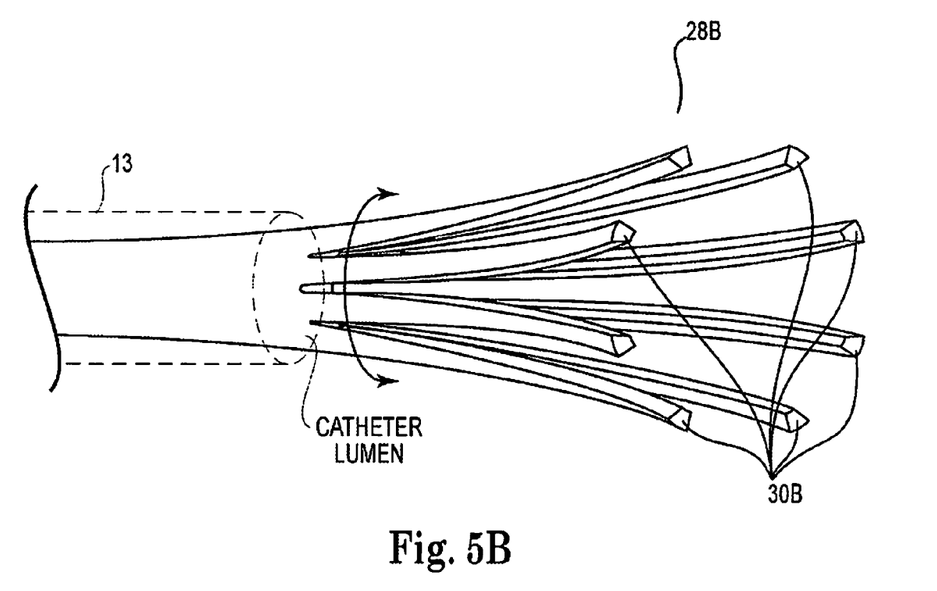
FIG. 5B is a partial cutaway side view of one embodiment of the present invention.

FIGS. 5A and 5B illustrate another embodiment of the automatically expanding ablating element 28B. This embodiment comprises at least two radially expandable fingers 30B formed by longitudinal slots 29 on either side of each finger 30A. The individual fingers 30B are shown in a first deformed and retracted position in FIG. 5A, with each finger 30B collapsed against and disposed adjacent two other fingers 30B, without overlap or interleaving. Thus, the ablating element 28B comprises a first deformed and retracted position profile having a diameter and profile that is comparable with that of drive shaft 20; as with the previously discussed embodiment, the maximum diameter will be that of the inner diameter of the catheter lumen. The ablating element 28B may comprise a separately manufactured element that is subsequently fixedly attached to the most distal end of drive shaft 20. Such a configuration may comprise a tube 32 that is fixedly attached to the distal end of drive shaft 20, with the ablating element 28B and its fingers 30B formed from and defined by tube 32. Alternatively, ablating element 28B may not comprise tube 32, wherein the ablating element is separately manufactured and subsequently attached directly to distal end of drive shaft 20.

Thus, the illustrated configurations and embodiments of FIGS. 5A and 5B allow the deformed and retracted ablating element 28B to achieve a retracted profile that is comparable with that of drive shaft 20 and/or tube 32 (when present) proximal to the ablating element 28B in terms of its diameter, thereby enabling the deformed and retracted ablating element 28B to fit within the lumen of catheter 13 while allowing the necessary rotatability and axial translatability between catheter 13 and drive shaft 20 and the ablation element 28B. At a maximum retracted diameter, ablating element 28B will approximate the internal diameter of catheter lumen as ablating element 28B is constrained by catheter lumen.

Extension by the operator of the ablating element 28B beyond the distal end of catheter 13 automatically allows expansion of the ablating element 28B to a second expanded position as the fingers 30B expand either to the maximum preset diameter and state or up to the point where the fingers 30B encounter either the vessel wall or the occluding material. Ablating element 28B experiences an elastic and non-plastic deformation to achieve the second expanded position within the subject lumen; the various mechanisms and methods for achieving this automatic elastic and non-plastic deformative expansion are discussed above in connection with FIGS. 3A and 3B. Thus, as also discussed briefly above, the expanded diameter of the ablating element 28B in the second expanded position is sufficient to accommodate vessels having diameters as large as 9 mm. Thus, the ablating element 28B is preferably constructed so that, when released from deformation, it automatically moves to assume a position that is in a pressing and atraumatic operative engagement with the inner lumen wall.

Thus, at least a portion of the fingers 30B operatively press against the inner wall of the lumen, more preferably against occluding material within the lumen. This creates an opposing biasing force that is transmitted to, and ultimately exerted by, the outer the fingers 30B against the inner wall of the lumen, preferably in close proximity to the occluding material that is to be directionally ablated. In this manner, the cutting edge and grinding surface are biasingly forced against the occluding material in preparation for directional rotational ablation, i.e., cutting and/or grinding.

In practice, a preferred embodiment of the present invention comprises all embodiments of ablating element 28, including embodiment 28B, in the retracted position sized to fit within the lumen of a 6 French introducer tube 13. This retracted position thus allows all embodiments of the ablating element 28 described herein to be positioned via and within introducer tube 13 near occluding material without causing unnecessary trauma during insertion via the patient's vasculature.

Figure 5C:
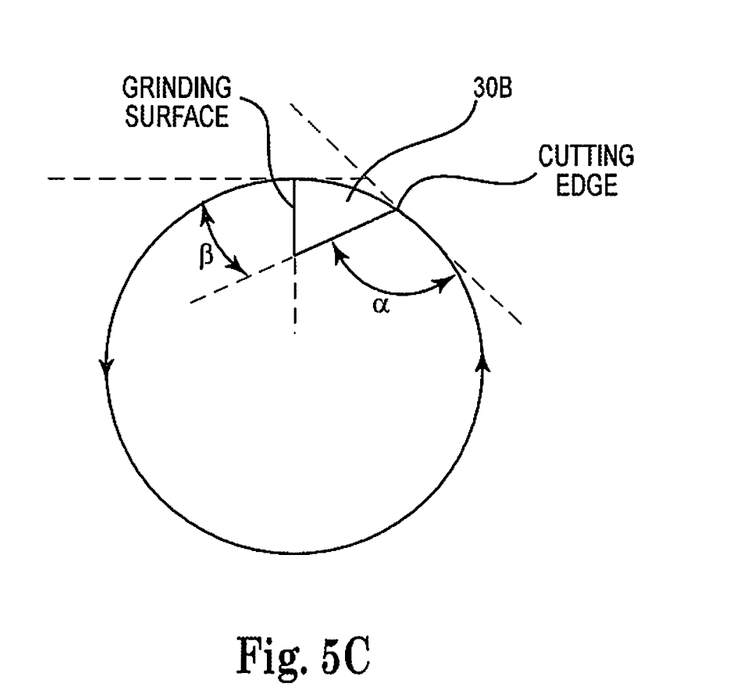
FIG. 5C illustrates an end view of one embodiment of the present invention, wherein the angles of the grinding surface and the cutting edge are provided.

FIG. 5C illustrates an end view of one of the fingers 28B located on an exemplary rotational path. Each finger 28B comprises a grinding surface and a cutting edge. The grinding surface may comprise abrasive, e.g., diamond dust or etching of the surface as is well known in the art. By way of example, the abrasive material may be any suitable material, such as diamond powder, fused silica, titanium nitride, tungsten carbide, aluminum oxide, boron carbide, or other ceramic materials. The abrasive material may comprise diamond chips (or diamond dust particles) attached and/or coated directly to the outer surface 36, such attachment may be achieved using well known techniques, such as conventional electroplating or fusion technologies (see, e.g., U.S. Pat. No. 4,018,576) and as further described above.

Alternately the grinding surface may comprise a grinding surface which has been roughened to provide a suitable abrasive surface. In yet another variation, the grinding surface may be etched or cut (e.g., with a laser) to provide small but sharp cutting surfaces. Other similar techniques may also be utilized to provide a suitable grinding surface and as further described above.

In the illustrated embodiment, the cutting edge comprises angle $\alpha$ while grinding surface further comprises an angle $\beta$. Angle $\beta$ forms a normal angle, defined by the angle of intersection of the face of the grinding surface and a line tangent to the rotational tracing circle illustrating the rotation of the grinding surface tip. The cutting edge comprises angle $\alpha$ which, in contrast, forms an obtuse angle, defined by the angle of intersection of the cutting edge and a line tangent to a circle formed by the cutting edge's tip during rotation; the rotational tracing circle illustrated. Consequently, the grinding surface does not cut, rather the grinding surface grinds and/or sands the occluding material. Similarly, the cutting edge does not grind and/or sand, but instead cuts the occluding material.

Thus, the embodiments of ablating element 28 discussed supra all comprise a mechanism for automatic expansion from a first deformed and retracted position to a second expanded position as described herein. Each illustrated embodiment provides a symmetric profile when viewed from the distal end of ablating element 28, when either in second expanded or in first deformed and retracted positions. However, it is well within the scope of the present invention to provide an ablating element 28 that expands to an asymmetric second expanded position, such as shown schematically in FIG. 5F. Such an asymmetric second expanded position may be achieved by an exaggerated material preset of one or more fingers 30 when compared with other fingers 30, or by differential application of heat and/or cold to selected fingers 30 as those processes are described above. In such an embodiment, rapid rotation of the asymmetrically expanded ablating element 28 may result in a wobbling or orbital motion of ablating element 28. This motion will result in a rotational, working, diameter for the ablating element 28 that is greater than its resting, expanded diameter. This is advantageous since it may allow introduction of a smaller diameter catheter 13, drive shaft 20 and ablating element 28, allowing for greater patient comfort and less trauma during traversing of the patient's vasculature.

Further, the ablating element 28 which automatically expands to a non-deformed position may be manipulated by the operator to initially comprise an asymmetric (or symmetric) profile achieved through processes described herein, e.g., application of heat and/or cold either differentially to select fingers and/or in combination with the material preset default expansions, wherein ablation occurs, followed by conversion through the processes described herein to a symmetric (or asymmetric) profile.

Figure 5D:
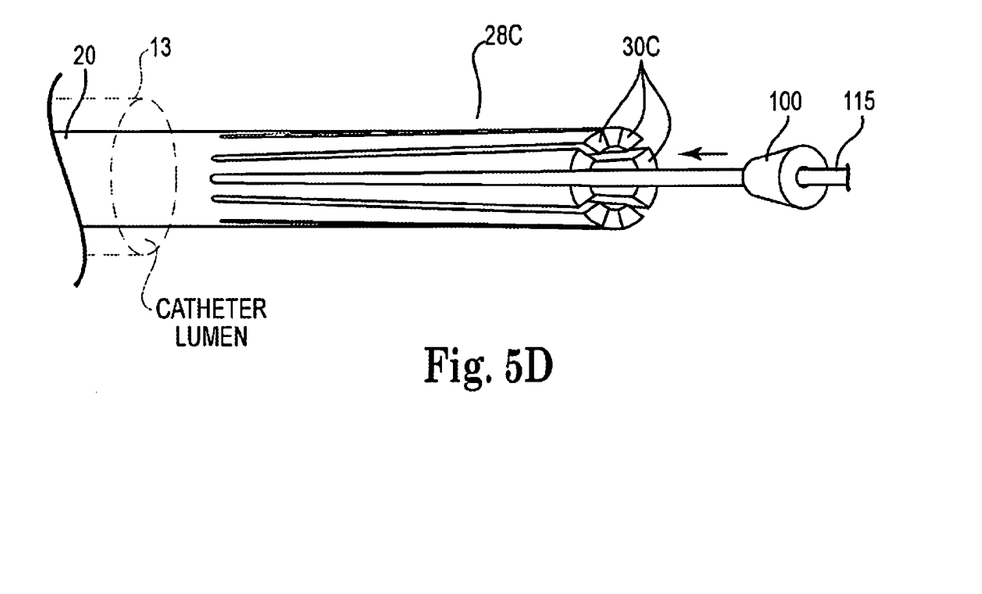
FIG. 5D is a partial cutaway side view of one embodiment of the present invention.
Figure 5E:
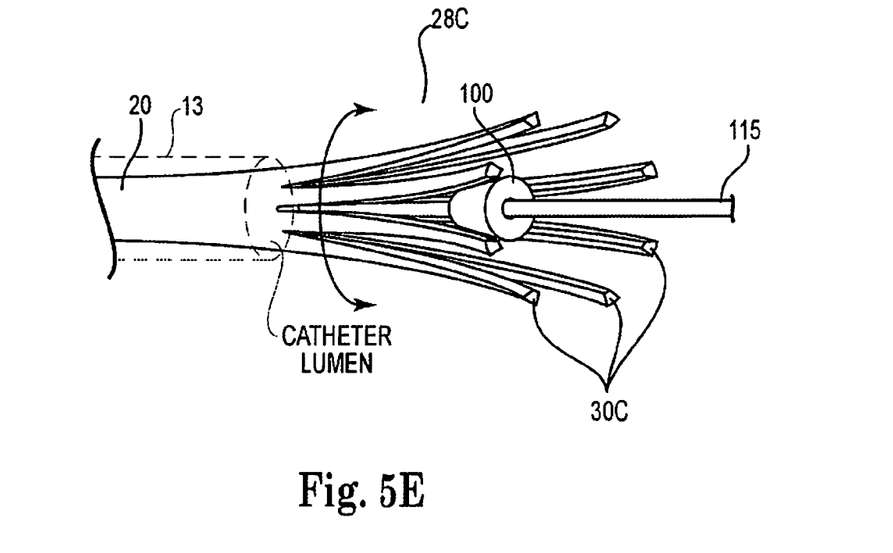
FIG. 5E is a partial cutaway side view of one embodiment of the present invention.
Figure 5F:
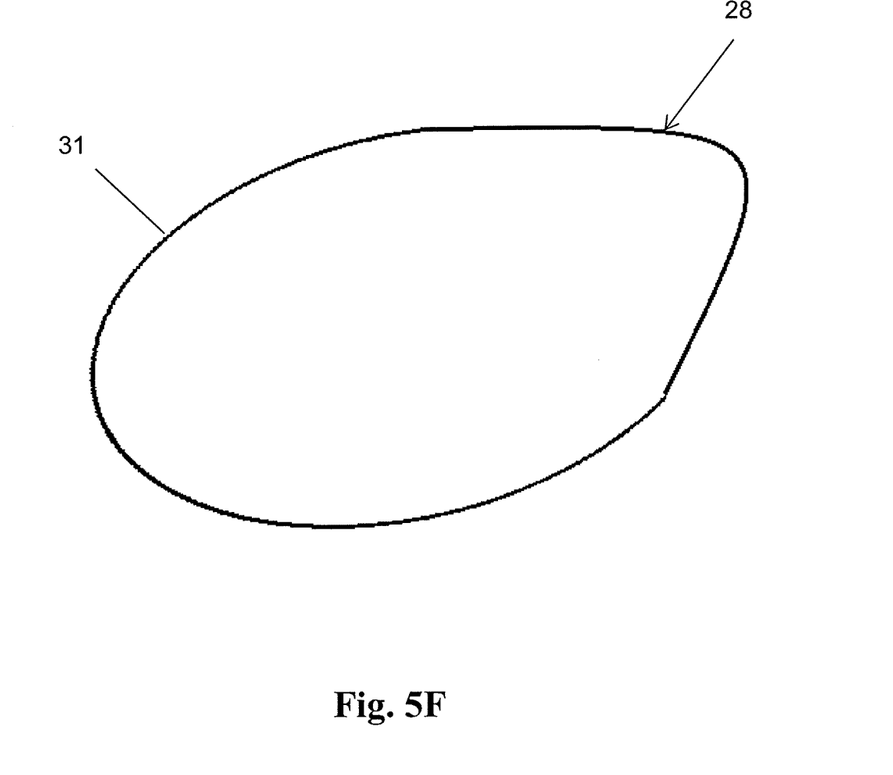
FIG. 5F illustrates an end view of one embodiment of the invention, wherein the ablating element is in the undeformed expanded position.

FIGS. 5D-5E illustrate still another alternative embodiment of ablating element 28, wherein the first retracted position is undeformed and the second expanded position is deformed. Thus, drive shaft 20 is shown axially translated distally beyond the constraints of catheter 13 and its lumen. Fingers 30C, however, remain in the first retracted position as they do not automatically expand when released from catheter's lumen. Consequently, an actuating device 100 is required to urge the fingers 30C radially outward. One embodiment of such an actuating device 100 is shown as a wedge 100 attached to a wire or string 115 that is translatable distally and proximally by the operator. The wedge 100 is shown as having a smaller proximal diameter than its distal diameter. As a consequence, the further the wedge 100 is pulled in the proximal direction by the operator, the more radial expansion of the fingers 30C is achieved as shown in FIG. 5E. In this manner, the degree and amount of radial expansion of the fingers 30C may be controlled by the operator. As with all embodiments discussed herein, the ablating element 28C is bi-directionally rotatable, with each finger comprising a grinding surface with an approximately normal or slightly obtuse angle to a line tangent to its rotational tracing circle and a cutting edge comprising an obtuse angle to a line tangent to its rotational tracing circle.

The actuating device 100 is illustrated as a wedge, however the skilled artisan will recognize that a number of variations of this structure exist, each of which are within the scope of the present invention. For example, the wedge illustrated is symmetric in profile, i.e., approximately a perfect circle, which results in a symmetric expansion of the fingers 28C. An alternative is to provide an asymmetric wedge, i.e., not a perfect circle in profile, which will result in an asymmetric expansion of the fingers 28C when the wedge 100 is pulled proximally back into the fingers 30C. Rapid rotation of the asymmetrically expanded fingers 28C may result in a rotational diameter that is larger than its resting, expanded diameter. This may be desirable since a smaller diameter catheter 13, drive shaft 20 and ablating element 28 may be introduced into the patient's vasculature, thereby reducing discomfort and trauma while maximizing ablating diameter.

Similarly, the actuating device 100 may comprise a balloon, either symmetric to achieve a symmetric second deformed and expanded position, or asymmetric to achieve an accordingly asymmetric second deformed and expanded position. Other equivalent actuating device 100 structures will certainly occur to the skilled artisan; each such equivalent structure is within the scope of the present invention.

Moreover, the structure of the various embodiments of fingers 30 is illustrated herein as generally radiused in outer transverse cross section. This is a preferred cross-sectional profile since it approximates the radiused profile of the vessel, however alternate shapes and profiles may present themselves to those skilled in the art. For example, elliptical, rectangular, square, and polygonal transverse cross-sectional profiles may be used with success for the ablating element 30. Each such alternate embodiment is within the scope of the present invention.

For all embodiments of ablating element 28, an additional method to create asymmetry for the expanded position may comprise the fingers 30 having differential masses. Accordingly, one or more than one finger 30 may be at least partially formed of a material having a density that is greater than the density of the remaining fingers 30. In this way, the center of mass of ablating element 28 may be moved radially away from the longitudinal axis A shown in FIG. 2. Accordingly, high-speed rotation of asymmetric ablating element 28 when expanded may result in an orbital wobbling of the element 28, wherein the working expanded and rotating diameter of the element 28 is greater than its resting expanded diameter.

The structure of the present invention having been described in detail, we now turn to discussion of methods of use of the present invention and its operation.

The procedure may begin with inserting a guide wire 15 to a position proximate the occluding material. An introducer catheter 13 may be provided with guide wire 15 within lumen of introducer catheter 13, to a position proximal the occluding material. The guide wire 15 may be withdrawn and catheter tube 20 may be introduced through introducer catheter's 13 lumen. Catheter tube 20 comprises the ablating element 28 of the present invention, including biasing element 30 and cutting element 32. When ablating element 28 as illustrated in FIG. 2, and including all embodiments discussed herein, is retained within catheter tube 20 lumen, it will be in retracted position, with biasing element 30 in a deformed substantially linear alignment with longitudinal axis A.

The ablating element 28 may be extended distally from the confines of the lumen of introducer catheter 13 which may result in automatic expansion of ablating element 28 to pressingly and atraumatically engage the occluding material within vessel wall.

When the expanded position is achieved, the operator may rotate the ablating element 28, resulting in engagement of the occluding material by the cutting edge. Further, rotation of ablating element 28 in the opposite direction may result in grinding surface grinding and/or sanding occluding material.

Such rotation may occur at very low to reasonably high rotational speeds enabled by the apparatus of FIG. 1, or the operator may rotate the ablating element 28 by hand. Alternatively, manual or automated reciprocating rotational and/or axial movement may allow focused directional ablation of a specific region of the subject lumen and/or allow biased ablation of the entire circumference of the subject lumen. Alternative reciprocating methods may comprise rotational reciprocation of less than one full revolution or rotational reciprocation of one full revolution or rotational reciprocation of more than one full revolution. Still more alternatively, rotational motion may be converted into translational motion for this, and all embodiments described herein, through use of a cam mechanism in the device's handle, a mechanical structure well known to the skilled artisan. In this manner, vibrational energy and movement may be created in the axial direction.

Further, the operator may move the expanded ablating element 28 axially, proximally and/or distally, to engage the distal cutting edge 34 to enhance the ablating process while the shape of lip 33 protects the vessel wall from the cutting edge 34. This axial movement may be achieved by manual proximal and/or distal movement of the ablating element 28 and/or by high-frequency vibration provided by, e.g., a piezo motor in operative communication with ablating element 28 as will be well understood by the skilled artisan. Automated axial movement may be achieved using motorized devices well known to the skilled artisan for applying force in a distal direction on the ablating element 28. Automated axial reciprocating movement, i.e., alternating application of proximal and distal force, may also be used. Alternatively, a piezo actuator may be positioned near the ablating element 28 and in operative communication with a conductive wire which energizes the piezo actuator, there by causing the actuator to change length at a high frequency and resulting in high-frequency vibration and axial movement of distal cutting edge 34 through occluding material. Such piezo actuator may, for example, be operationally connected with the catheter tube 20, effectively creating a piezotube for high-frequency vibration of the ablating element 28 and distal cutting edge 34.

When the occluding material is sufficiently cleared away, the operator may then retract the expanded ablating element 28 proximally into the lumen of introducer catheter 13, thus retracting ablating element 28 to its retracted position for withdrawal from the patient.

Alternatively, the introducer catheter 13 may not be required in the embodiment where the expanded and retracted positions of the ablating element 28 are achieved using alternating heating and cooling, i.e., either by perfusion of controlled temperature liquid, e.g., saline, or by application of electrical current.

Thus, a method of directionally clearing target tissue comprising occluding material within a lumen using the present invention may comprise:

providing a catheter tube having an outer diameter smaller than the lumen and having an ablating element in a first deformed retracted position at the distal end of the catheter tube;

advancing the catheter tube through the lumen to a position proximate the occluding material;

urging the deformed retracted ablating element into an undeformed expanded second position, wherein the fingers of ablating element comprise a cutting edge having an obtuse angle and a grinding surface;

allowing the cutting edge to engage the occluding material by rotating in the cutting direction;

allowing the grinding surface to engage the occluding material to engage the occluding material by rotating in the cutting direction;

allowing only the grinding surface to engage the occluding material by rotating in the grinding direction;

urging the expanded ablating element into its deformed retracted position; and withdrawing the retracted ablating element from the lumen.

Alternative methods will comprise the modifications of, inter alia, one or more of the ablating element 28 comprising a symmetric or asymmetric expanded shape; comprising an actuating device 100 to achieve a second, deformed and expanded position wherein the actuating device 100 and the second, deformed and expanded position are either symmetric or asymmetric.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A rotational atherectomy device for ablation of occluding material in a blood vessel having a diameter, comprising:
    a catheter having an outer diameter less than the diameter of the blood vessel and a lumen therethrough and further comprising a distal end and a longitudinal axis;
    a rotatable drive shaft having a lumen therethrough and rotatable and axially translatable within the lumen of the catheter; and
    an ablating element attached to the distal end of the rotatable drive shaft, comprising more than one flexible finger, each flexible finger comprising:
        a cutting edge, the cutting edge having an obtuse angle as defined by the angle of intersection of the cutting edge and a line tangent to a circle formed by the cutting edge's tip during rotation;
        an inner surface,
        an external surface having a grinding surface thereon, the grinding surface forms a normal angle defined by the angle of intersection of the grinding surface and a line tangent to a circle formed by the grinding surface's tip during rotation, and
        a thickness between the inner surface and the external surface;
        the ablating element having at least a deformed retracted position when constrained within the lumen of the catheter and an undeformed expanded position, wherein the deformed retracted position comprises a symmetric profile and the undeformed expanded position comprises an asymmetric profile, wherein the undeformed asymmetric expanded position is achieved by increasing the temperature differentially to select fingers of the ablating element.

2. The rotational atherectomy device of claim 1, further comprising a rotating means, whereby the ablating element may be rotated to cut and to grind when rotated in one direction and grind when rotated in the opposite direction.

3. The rotational device of claim 1, further comprising the expanded asymmetric ablating element having a resting diameter and a rotating diameter, wherein the resting diameter is less than the rotating diameter.

4. The rotational atherectomy device of claim 1, wherein the more than one flexible finger of the ablating element comprises a shape memory alloy.

5. The rotational atherectomy device of claim 1, wherein the retracted position of the ablating element comprises a diameter of 6 French and the expanded position of the ablating element comprises a diameter of 9 mm.

6. The rotational atherectomy device of claim 1, further comprising a piezo device in operative communication with the ablating element, wherein actuation of the piezo device results in ablation by high-frequency vibration of the ablating element.

7. A rotational atherectomy device for ablation of occluding material in a blood vessel having a diameter, comprising:
   a catheter having an outer diameter less than the diameter of the blood vessel and a lumen therethrough and further comprising a distal end and a longitudinal axis;
   a rotatable drive shaft having a lumen therethrough and rotatable and axially translatable within the lumen of the catheter; and
   an ablating element attached to the distal end of the rotatable drive shaft, comprising more than one flexible finger, each flexible finger comprising:
      a cutting edge, the cutting edge having an obtuse angle as defined by the angle of intersection of the cutting edge and a line tangent to a circle formed by the cutting edge's tip during rotation;
      an inner surface,
      an external surface having a grinding surface thereon, the grinding surface forms a normal angle defined by the angle of intersection of the grinding surface and a line tangent to a circle formed by the grinding surface's tip during rotation, and
      a thickness between the inner surface and the external surface;
   the ablating element having at least a deformed retracted position when constrained within the lumen of the catheter and an undeformed expanded position, wherein the deformed retracted position comprises a symmetric profile and the undeformed expanded position comprises an asymmetric profile, wherein the undeformed asymmetric expanded position is achieved by decreasing the temperature differentially to select fingers of the ablating element.

8. The rotational atherectomy device of claim 7, further comprising a rotating means, whereby the ablating element may be rotated to cut and to grind when rotated in one direction and grind when rotated in the opposite direction.

9. The rotational device of claim 7, further comprising the expanded asymmetric ablating element having a resting diameter and a rotating diameter, wherein the resting diameter is less than the rotating diameter.

10. The rotational atherectomy device of claim 7, wherein the more than one flexible finger of the ablating element comprises a shape memory alloy.

11. The rotational atherectomy device of claim 7, wherein the retracted position of the ablating element comprises a diameter of 6 French and the expanded position of the ablating element comprises a diameter of 9 mm.

12. The rotational atherectomy device of claim 7, further comprising a piezo device in operative communication with the ablating element, wherein actuation of the piezo device results in ablation by high-frequency vibration of the ablating element.

* * * * *